(12) United States Patent
Pecherer et al.

(10) Patent No.: US 8,162,826 B2
(45) Date of Patent: Apr. 24, 2012

(54) LARYNGOSCOPES AND RECHARGEABLE ILLUMINATION UNITS FOR USE THEREWITH

(75) Inventors: Eugeny Pecherer, Netanya (IL); Igor Kobets, Pardess Hanna (IL)

(73) Assignee: Truphatek International Ltd., Netanya (IL)

( * ) Notice: Subject to any disclaimer, the term of this patent is extended or adjusted under 35 U.S.C. 154(b) by 204 days.

(21) Appl. No.: 12/450,009

(22) PCT Filed: Mar. 11, 2008

(86) PCT No.: PCT/IL2008/000328
§ 371 (c)(1),
(2), (4) Date: Sep. 8, 2009

(87) PCT Pub. No.: WO2008/111057
PCT Pub. Date: Sep. 18, 2008

(65) Prior Publication Data
US 2010/0022843 A1  Jan. 28, 2010

(30) Foreign Application Priority Data
Mar. 11, 2007 (IL) .......................................... 181851

(51) Int. Cl.
*A61B 1/267* (2006.01)
(52) U.S. Cl. ...................................................... 600/197
(58) Field of Classification Search ........... 600/184–199
See application file for complete search history.

(56) References Cited

U.S. PATENT DOCUMENTS

| 2,433,705 A | 12/1947 | Palmeter |
| 3,426,749 A | 2/1969 | Jephcott |
| 3,598,113 A | 8/1971 | Moore |
| 3,766,909 A | 10/1973 | Ozbey |
| 3,826,248 A | 7/1974 | Gobels |
| 3,856,001 A | 12/1974 | Phillips |
| 4,037,588 A | 7/1977 | Heckele |
| 4,406,280 A | 9/1983 | Upsher |
| 4,437,458 A | 3/1984 | Upsher |
| 4,527,553 A | 7/1985 | Upsher |
| 4,556,052 A | 12/1985 | Muller |
| 4,557,256 A | 12/1985 | Bauman |

(Continued)

FOREIGN PATENT DOCUMENTS

DE     26 21 232     11/1977
(Continued)

OTHER PUBLICATIONS

Hilbro brochure, Green System Fiber Optic Laryngoscope, Interchangeable Light Guide Insert, Oct. 2001.

(Continued)

*Primary Examiner* — Eduardo C Robert
*Assistant Examiner* — Stuart S Bray
(74) *Attorney, Agent, or Firm* — Abraham Hershkovitz; Harold L. Novick; Hershkovitz & Associates LLC (57) ABSTRACT

Laryngoscope handles including a handle shell having a pair of opposite semi-cylindrical metal or plastic handgrip support members permanently joined together to form a tubular handgrip support and a non-metal sleeve-like handgrip encircling the handgrip support. Rechargeable illumination units for use with laryngoscopes and including a light transmissive end cap diffusely glowing on interior illumination by a least one user indication light source for providing at least one visual user indication regarding the operability of an illumination unit.

20 Claims, 6 Drawing Sheets

U.S. PATENT DOCUMENTS

| | | | |
|---|---|---|---|
| 4,565,187 A | 1/1986 | Soloway | |
| 4,570,614 A | 2/1986 | Bauman | |
| 4,579,108 A | 4/1986 | Bauman | |
| 4,583,527 A | 4/1986 | Musicant et al. | |
| 4,596,239 A | 6/1986 | Bauman | |
| 4,679,547 A | 7/1987 | Bauman | |
| 4,878,486 A | 11/1989 | Slater | |
| 4,884,558 A | 12/1989 | Gorski et al. | |
| 4,930,495 A | 6/1990 | Upsher | |
| 4,958,624 A | 9/1990 | Stone et al. | |
| 4,972,825 A | 11/1990 | Vescovo, Jr. | |
| 5,060,633 A | 10/1991 | Gibson | |
| 5,065,738 A | 11/1991 | Van Dam | |
| 5,178,131 A | 1/1993 | Upsher | |
| 5,355,870 A | 10/1994 | Lacy | |
| 5,501,651 A | 3/1996 | Bauman | |
| 5,529,570 A | 6/1996 | Storz | |
| 5,651,760 A | 7/1997 | Upsher | |
| 5,702,351 A | 12/1997 | Bar-Or et al. | |
| 5,879,304 A | 3/1999 | Shuchman et al. | |
| 6,013,026 A | 1/2000 | Krauter et al. | |
| 6,139,491 A | 10/2000 | Heine et al. | |
| 6,213,937 B1 | 4/2001 | Vivenzio | |
| 6,719,688 B2 | 4/2004 | Pecherer et al. | |
| 7,128,710 B1 | 10/2006 | Cranton et al. | |
| 7,214,184 B2 | 5/2007 | McMorrow | |
| 7,608,040 B1 * | 10/2009 | Dunst | 600/187 |
| 7,771,350 B2 * | 8/2010 | Geist et al. | 600/199 |
| 2002/0082477 A1 | 6/2002 | Kim | |
| 2003/0092967 A1 * | 5/2003 | Fourie et al. | 600/191 |
| 2004/0122292 A1 | 6/2004 | Dey et al. | |
| 2004/0127770 A1 | 7/2004 | McGrath | |
| 2004/0215062 A1 | 10/2004 | Dalle et al. | |
| 2005/0043590 A1 * | 2/2005 | Mazzei et al. | 600/188 |
| 2005/0090712 A1 | 4/2005 | Cubb | |
| 2007/0093693 A1 * | 4/2007 | Geist et al. | 600/199 |
| 2007/0129606 A1 * | 6/2007 | Pecherer | 600/193 |
| 2009/0065007 A1 * | 3/2009 | Wilkinson et al. | 128/205.27 |
| 2009/0112067 A1 * | 4/2009 | Baker | 600/199 |
| 2009/0209816 A1 * | 8/2009 | Nielsen et al. | 600/118 |
| 2009/0270684 A1 * | 10/2009 | Nielsen et al. | 600/193 |

FOREIGN PATENT DOCUMENTS

| | | |
|---|---|---|
| DE | 202 18 560 | 7/2003 |
| GB | 685741 | 1/1953 |
| GB | 806467 | 12/1958 |
| WO | WO 2006/131770 | 12/2006 |

OTHER PUBLICATIONS

Medizintechnik KaWe Germany, Laryngoscopes, Megalight F.O.

* cited by examiner

LARYNGOSCOPES AND RECHARGEABLE ILLUMINATION UNITS FOR USE THEREWITH

CROSS REFERENCE TO RELATED APPLICATIONS

This application is the National Stage of International Application No. PCT/IL2008/000328 filed on 11 Mar. 2008 in the English language and designating the United States, the entire contents of which are incorporated herein by reference.

FIELD OF THE INVENTION

The invention pertains to laryngoscopes and rechargeable illumination units for use therewith.

BACKGROUND OF THE INVENTION

Laryngoscopes can be generally classified into two types as follows: Single component laryngoscopes including a laryngoscope handle and a permanently mounted laryngoscope blade. Single component laryngoscopes can have rigid constructions or a laryngoscope handle with a pivotally mounted laryngoscope blade for selective manipulation into a transverse intubation position. Single component laryngoscopes are available in metal or plastic constructions.

Dual component laryngoscopes including a laryngoscope handle and an interchangeable laryngoscope blade. ISO 7376/1 compatible laryngoscopes have a blade mounted illumination source for providing illumination light at their blade tips for illumination purposes. ISO 7376/3 compatible laryngoscopes have a handle mounted illumination source for providing illumination light at their blade tips for illumination purposes. Dual component laryngoscopes are available with metal or plastic laryngoscope handles and metal or plastic laryngoscope blades.

Most laryngoscope manufacturers are beginning to supply laryngoscope sets including a rechargeable laryngoscope handle with either an interchangeable or non-interchangeable rechargeable illumination unit. Rechargeable laryngoscope handles having a base surface with a green LED indicator for indicating charging are now available. However, users typically have to be looking directly at such a LED indicator for determining whether it is illuminated.

SUMMARY OF THE INVENTION

The first aspect of the present invention is directed towards novel laryngoscope handles including a pair of opposite semi-cylindrical metal or plastic handgrip support members permanently joined together to form a tubular handgrip support and a non-metal sleeve-like handgrip encircling same. The handgrips can be formed from a wide range of hard plastic materials including inter alia ABS, PVC, and the like, and elastomeric materials including inter alia rubber, synthetic rubber, silicone rubber, and the like. The novel laryngoscope handles afford a low cost ergonomic sturdy construction suitable for the aforesaid types of single and dual component laryngoscopes. The laryngoscopes can be powered by one or more standard size batteries or rechargeable power sources.

The second aspect of the present invention is directed towards rechargeable laryngoscope handles having either an interchangeable or non-interchangeable rechargeable illumination unit including a light transmissive end cap which glows diffusely on interior illumination by at least one user indication light source for providing at least one visual user indication regarding the operability of an illumination unit. The light transmissive end caps afford mechanical protection for user indication light sources and better all round visibility thereby facilitating user appraisal of the operability of an illumination unit. The user indication light sources can be single or multiple color light sources. The rechargeable illumination units are suitable for the aforesaid types of single and dual component laryngoscopes.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE PRESENT INVENTION

Figure 1A:
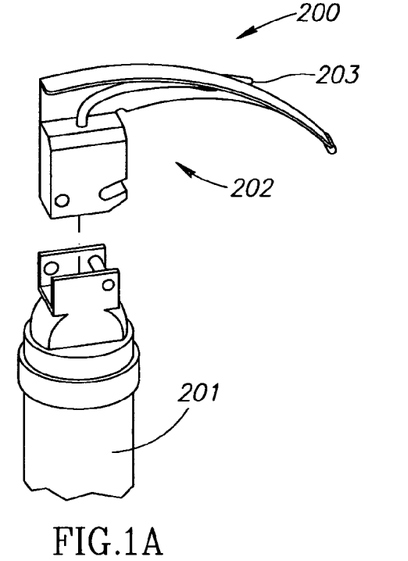
FIGS. 1A and 1B are perspective views of parts of two types of laryngoscopes.

FIGS. 1A, 1B, 1C and 1D show four types of laryngoscopes as follows:

First, in FIG. 1A there is depicted a dual component ISO 7376/1 compatible laryngoscope 200 including a laryngoscope handle 201 and an interchangeable laryngoscope blade 202 with a blade mounted illumination source 203 for selectively providing illumination light at the blade's tip for illumination purposes.

Figure 1B:
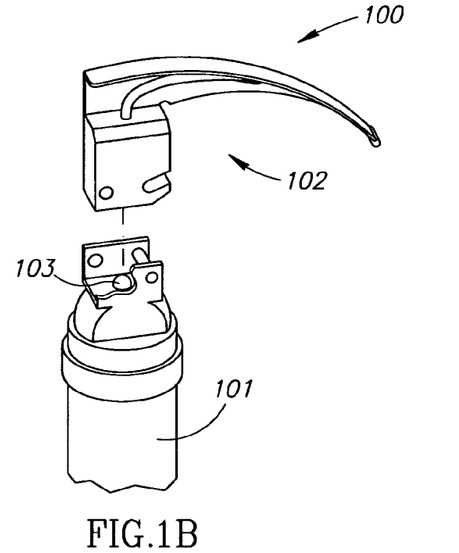

Second, in FIG. 1B there is depicted a dual component ISO 7376/3 compatible laryngoscope 100 including a laryngoscope handle 101 and an interchangeable laryngoscope blade 102 with the laryngoscope handle 101 including a handle mounted illumination source 103 for selectively providing illumination light at the blade's tip for illumination purposes.

Figure 1C:
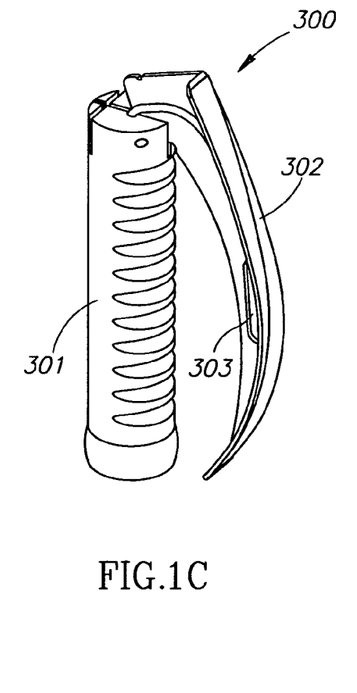
FIGS. 1C and 1D are perspective views of two complete, but different types of laryngoscopes, and a novel laryngoscope handle in accordance with the present invention.

Third, FIG. 1C shows a single component laryngoscope 300 including a laryngoscope handle 301 with a pivotally mounted laryngoscope blade 302 in a collapsed position which can be selectively manipulated into a transverse intubation position and having a blade mounted illumination source 303 for selectively providing illumination light at the blade's tip for illumination purposes.

Figure 1D:
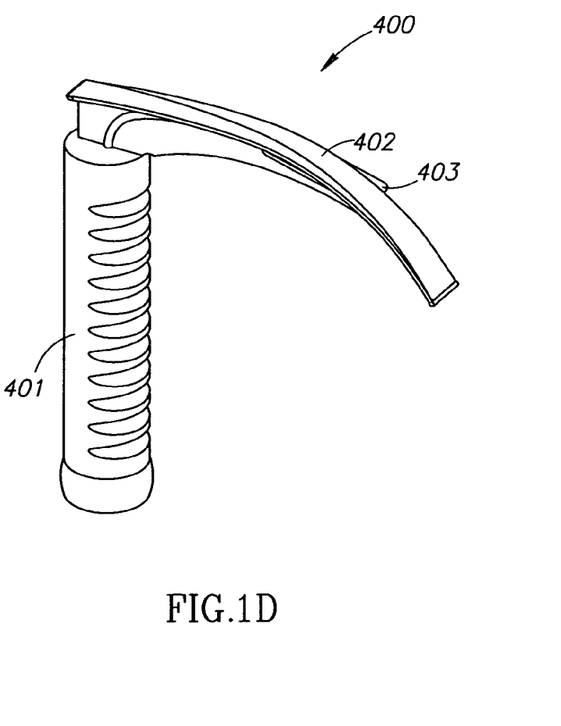

And fourth, in FIG. 1D there is depicted a single component laryngoscope 400 including a laryngoscope handle 401 with a rigidly mounted laryngoscope blade 402 in a transverse intubation position and having a blade mounted illumination source 403 for selectively providing illumination light at the blade's tip for illumination purposes. The laryngoscopes 100, 200, 300 and 400 can be powered either by batteries or a rechargeable power source.

Figure 2:
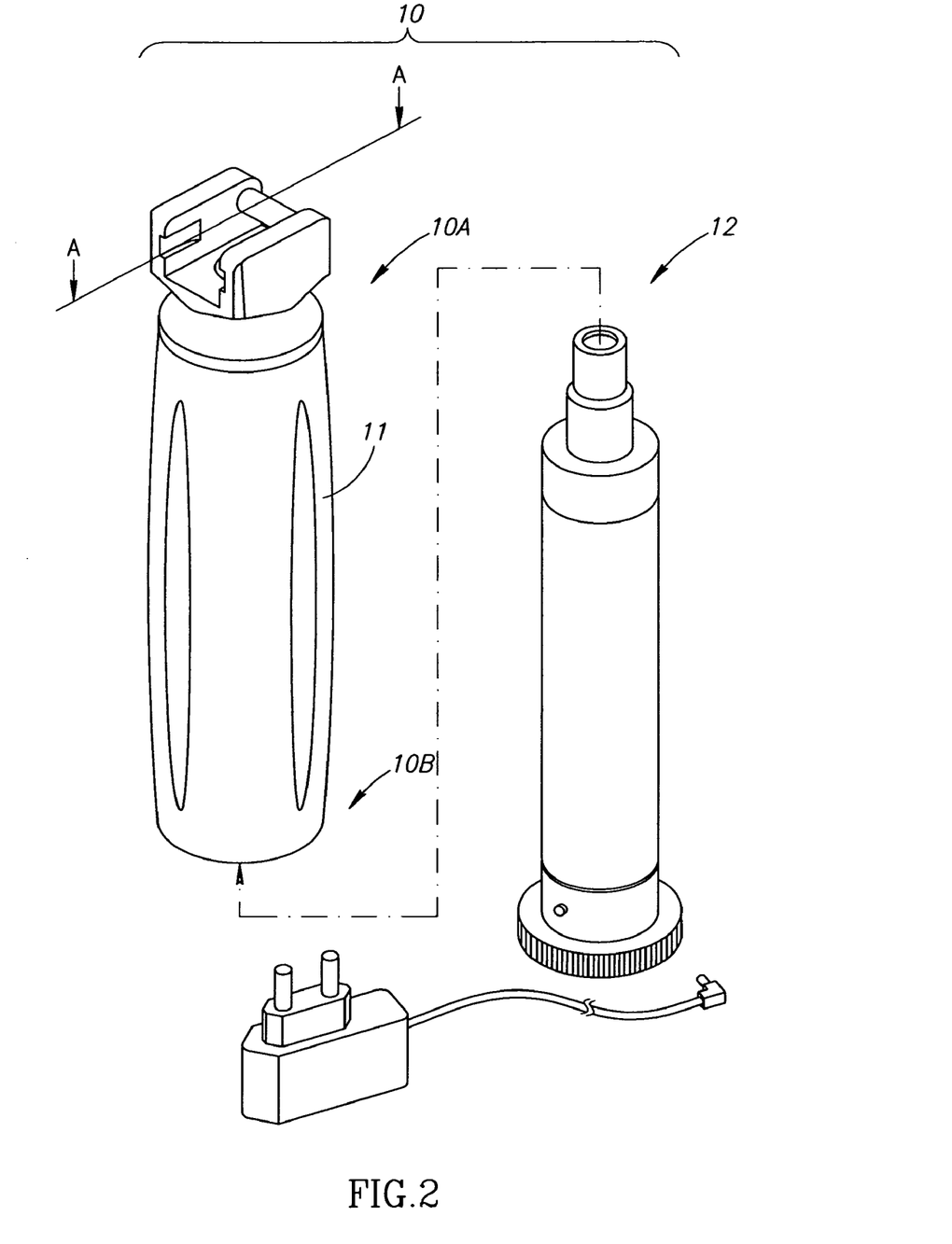
FIG. 2 is a dissembled view of an ISO 7376/3 laryngoscope handle including a handle shell and an interchangeable rechargeable illumination unit, and a mains charger for charging the batteries of an illumination unit.

FIG. 2 shows an ISO 7376/3 compatible laryngoscope handle 10 includes opposite leading and trailing ends 10A and 10B correspondingly adjacent and remote a conventional ISO 7376/3 compatible laryngoscope blade on snap fitting thereon. The laryngoscope blade 10 includes an open bottom handle shell 11 and an interchangeable rechargeable illumination unit 12 for sliding insertion into the handle shell 11. The illumination unit 12 can be recharged by a standard mains recharger with a male plug. The handle shell 11 is readily autoclavable for sterilization purposes on convenient removal of the illumination unit 12. The illumination unit 12 is typically not soiled during use.

Figure 3:
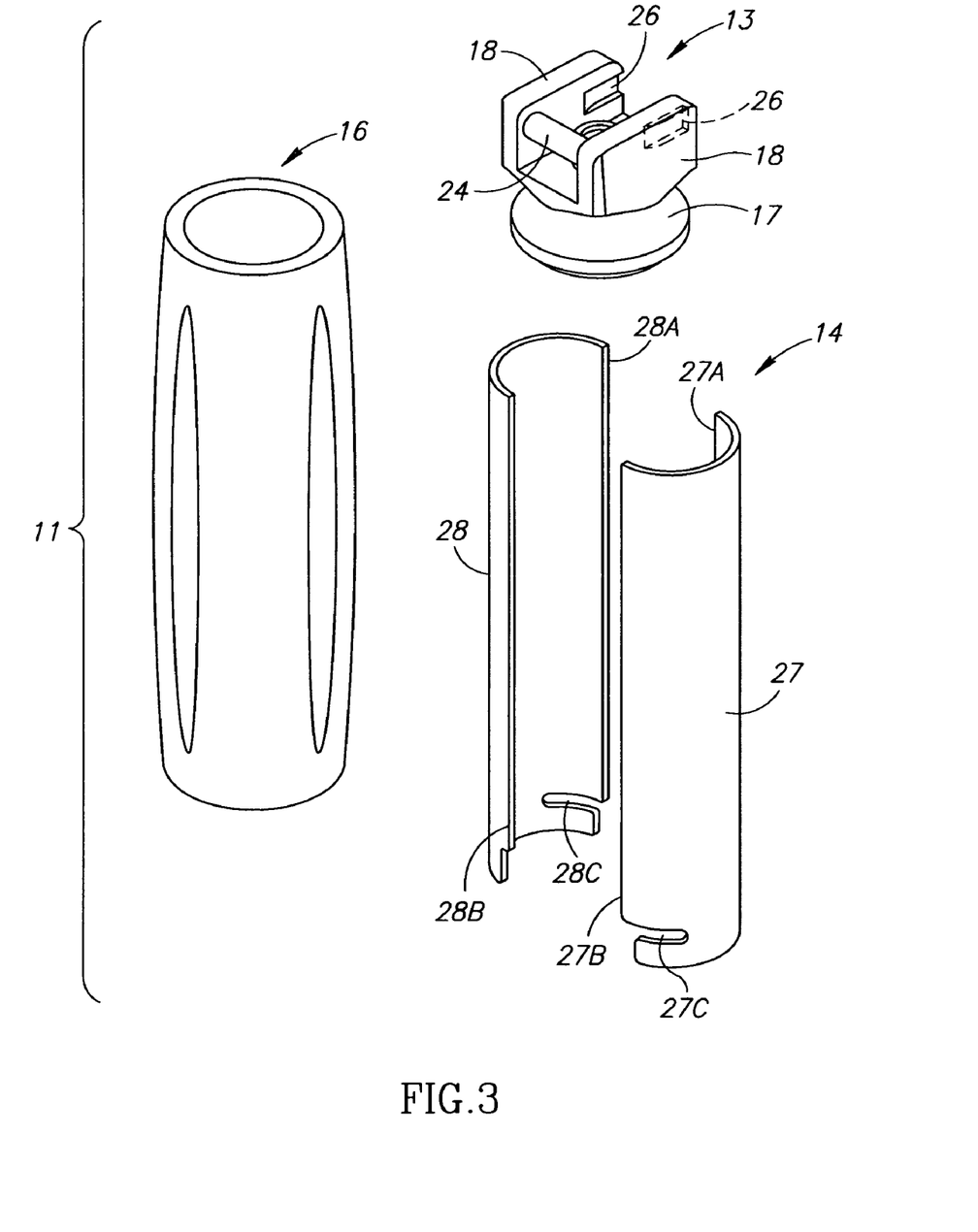
FIG. 3 is an exploded view of the handle shell depicted in FIG. 2.

FIG. 3 shows the handle shell 11 includes a conventional ISO 7376/3 compatible head 13 mounted on a tubular handgrip support 14 and a non-metal sleeve-like handgrip 16 for encircling the handgrip support 14. The handgrip 16 is preferably formed from hard plastic material, elastomeric material, and the like. The head 13 includes a base 17 and a pair of upright walls 18.

Figure 5:
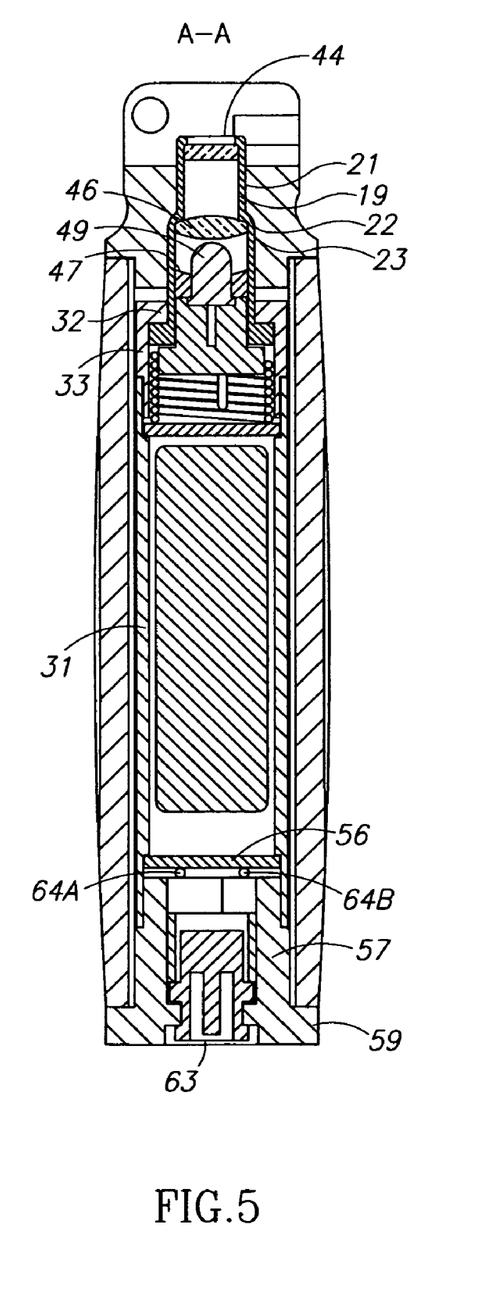
FIG. 5 is a longitudinal cross section of FIG. 2's ISO 7376/3 laryngoscope handle taken along line A-A in FIG. 2.

The base 17 is formed with a throughgoing bore 19 having a stepped cross section including a leading narrow diameter section 21, an intermediate shoulder 22, and a trailing wide diameter section 23 (see FIG. 5). The upright walls 18 are formed with a leading crossbar 24 extending therebetween, and a pair of opposite lateral grooves 26. A conventional ISO 7376/3 compatible laryngoscope blade snap fits onto the crossbar 24 and subsequently snap fits into the opposite grooves 26 for energizing the laryngoscope handle 10 for delivering illumination light for intubation purposes.

The handgrip support 14 is formed from a pair of identical semi-cylindrical handgrip support members 27 and 28. The handgrip support members 27 and 28 are formed from suitable rigid material including, for example, metal, engineering plastics, and the like. Suitable metals include inter alia stainless steel, and the like. Suitable engineering plastics include inter alia nylon, polysulphon, and the like. The handgrip support member 27 has a pair of longitudinal edges 27A and 27B, and a groove 27C at its lowermost end opposite the head 13. The handgrip support member 28 has a pair of longitudinal edges 28A and 28B, and a groove 28C at its lowermost end opposite the head 13 and opposite the groove 27C. The support members 27 and 28 are permanently joined together by appropriate assembly techniques, for example, brazing, ultrasonic welding, gluing, and the like.

Figure 4:
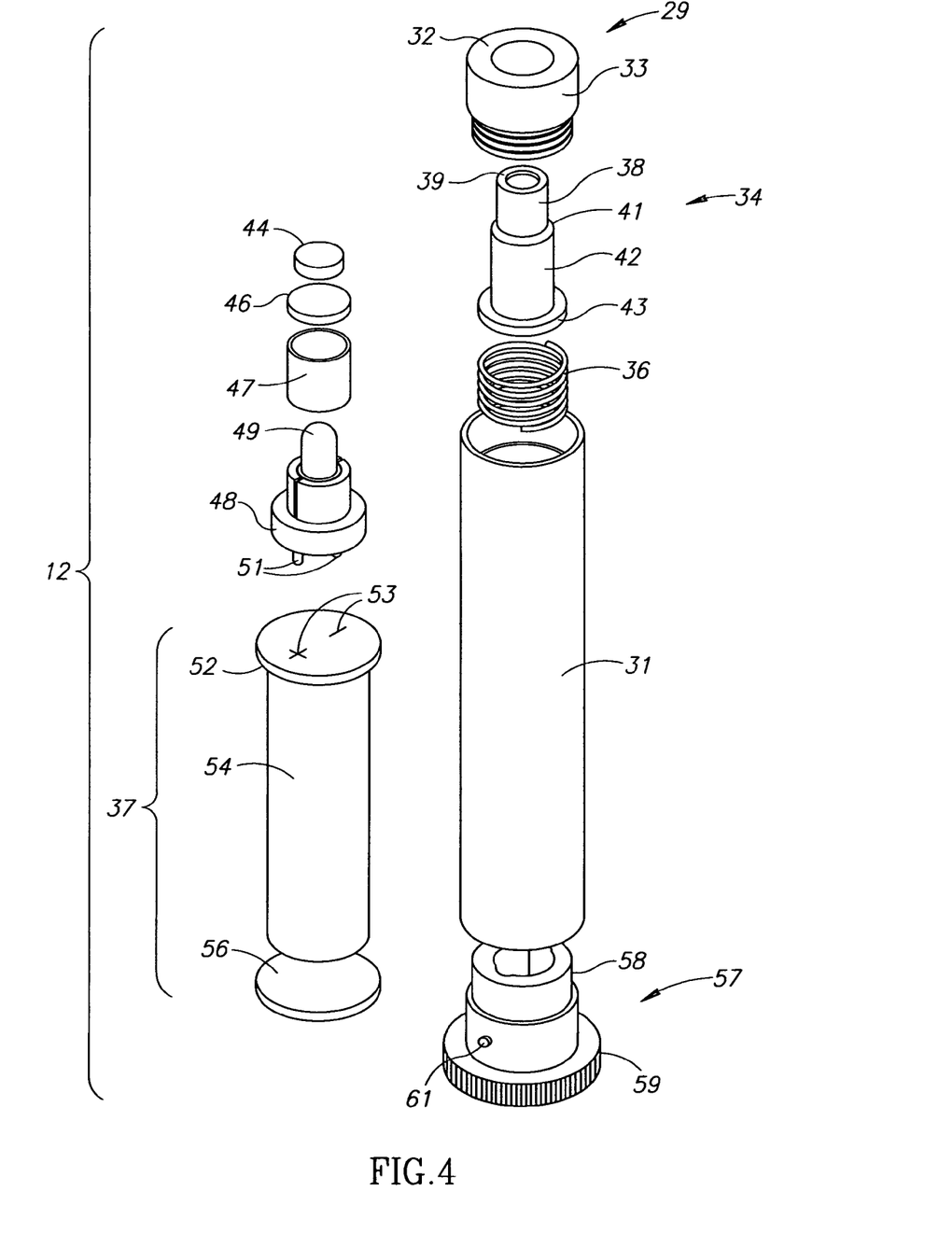
FIG. 4 is an exploded view of the illumination unit depicted in FIG. 2.
Figure 7:
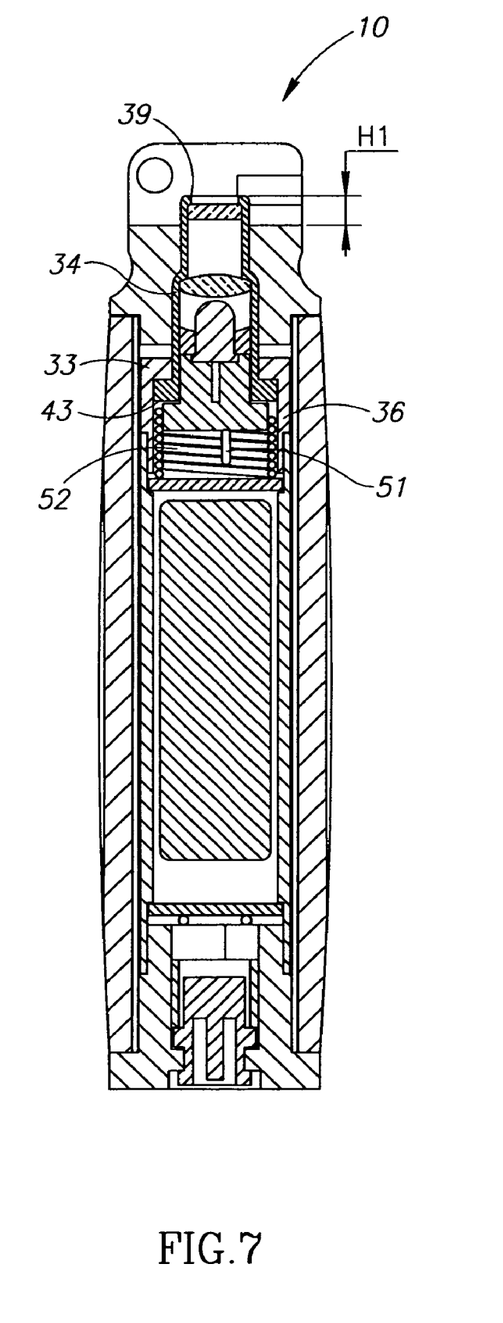
FIG. 7 is a longitudinal cross section of FIG. 2's ISO 7376/3 laryngoscope handle in a non-illuminating state along line A-A in FIG. 2.
Figure 8:
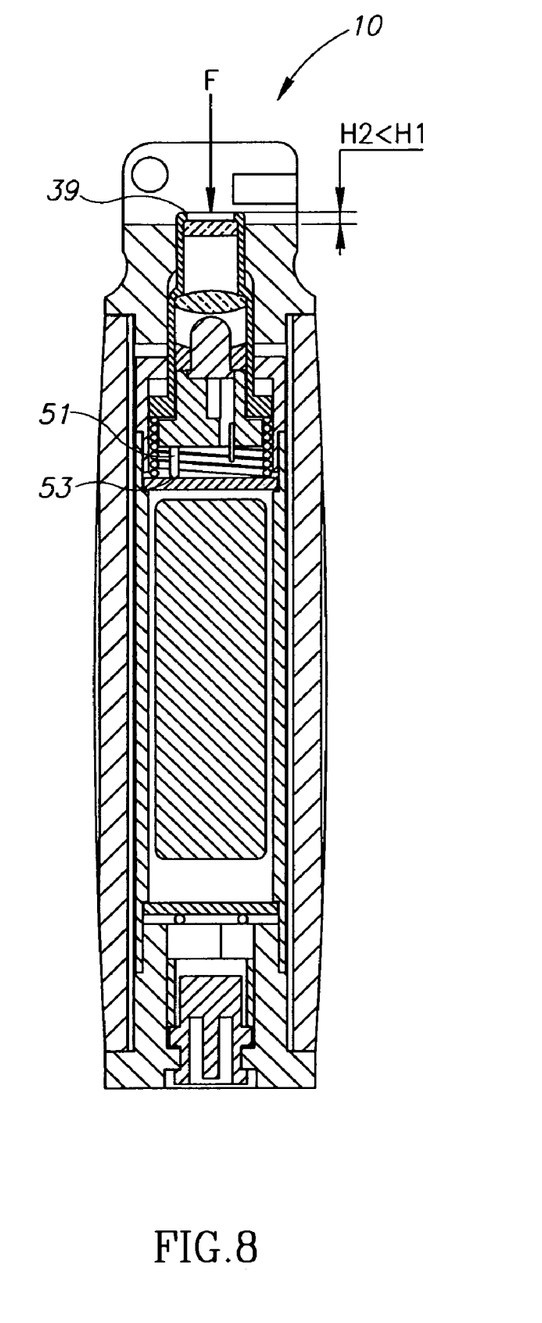
FIG. 8 is a longitudinal cross section of FIG. 2's ISO 731 '6/3 laryngoscope handle in an illuminating state taken along line A-A in FIG. 2.

FIGS. 4 and 5 show the illumination unit 12 includes a securing ring 29 mounted on an open ended cylindrical casing 31. The securing ring 29 has a leading annular flange 32, and a trailing cylindrical body 33 for mounting on the casing 31. The securing ring 29 houses an elongated cap 34 and a compression spring 36. The elongated cap 34 reciprocates in the throughgoing bore 19 between two extreme positions respectively corresponding to a non-illuminating state and an illuminating state of the laryngoscope handle 10 as shown in FIGS. 7 and 8, respectively.

The casing 31 houses a battery unit 37 rigidly mounted therein. The elongated cap 34 has a stepped cross section including a leading section 38 with a leading annular flange 39, an intermediate shoulder 41, a trailing section 42, and a lowermost outwardly directed flange 43. The leading section 38 houses a transparent window 44, and the trailing section 42 houses a convex lens 46, a reflector 47, and a Light Emitting Diode (LED) housing 48. The LED housing 48 includes a LED 49 for providing white illumination light at the laryngoscope handle's leading end 10A and downward depending positive and negative contact pins 51. The battery unit 37 includes a contact plate 52 with positive and negative contact pads 53 in registration with the contact pins 51, a rechargeable battery 54, and a charger module 56. The compression spring 36 is interdisposed between the elongated cap 34 and the contact plate 52 for biasing the elongated cap 34 away from the battery unit 37 stopped by the LED housing 48 abutting against the securing ring's flange 32.

The illumination unit 12 includes a light transmissive end cap 57 at the laryngoscope handle's trailing end 10B for sealing same. The light transmissive end cap 57 can be formed from suitable light transmissive plastic materials, for example, polycarbonate, transparent Perspex, and the like. The end cap 57 includes a leading cylindrical portion 58 for mounting into the casing 31 and a trailing base 59. The cylindrical portion 58 has a pair of outward radial pins 62 for bayonet fitting into the handgrip support's peripheral grooves 27C and 28C for removable mounting of the illumination unit 12 in the handle shell 11. The base 59 is formed with a female socket 63 in electrical connection with the charger module 56 and is intended to receive the mains recharger's male plug for charging the illumination unit 12.

Figure 6:
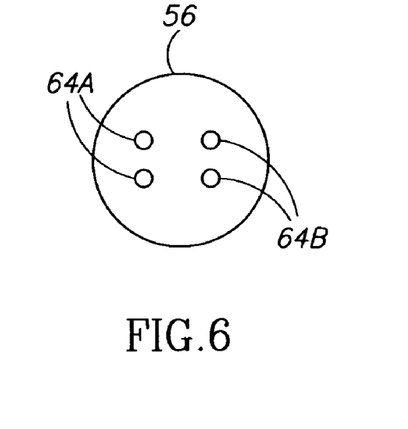
FIG. 6 is a bottom view of a charger module including user indication light sources.

FIG. 6 shows the charger module 56 includes user indication light sources 64 for selective illumination for providing visual user indications regarding the operability of the illumination unit 12. Illumination of the user indication light sources 64 causes the end cap 57 to glow diffusely thereby facilitating user appraisal of whether the light sources 64 are illuminated or not. In particular, the charger module 56 is operative to illuminate a pair of green LEDs 64A continuously during charging the laryngoscope handle 10 for indicating the battery unit 37 is charged to at least a predetermined minimum threshold. Additionally, the charger module 56 illuminates a pair of red LEDs 64B continuously during charging the laryngoscope handle 10 for indicating the battery unit 37 requires additional charging to reach the predetermined minimum threshold. And additionally, the charger module 56 flashes the red LEDs 64B on and off to indicate a fault condition, for example, the battery unit 37 is not correctly charging.

FIGS. 7 and 8 show the non-illuminating state and the illuminating state of the laryngoscope handle 10, respectively. In the non-illuminating state, the compression spring 36 urges the elongated cap 34 away from the battery unit 37 stopped by the LED housing 48 abutting against the securing ring's flange 32. In this position, the cap's leading annular flange 39 protrudes above the base 17 by a height H1 and the contact pins 51 are distanced from their counterpart contact pads 53, thereby breaking electrical contact between the LED 49 and the battery unit 37. On application of a downward force F on the cap's leading annular flange 39, the force F overcomes the compression spring 36 to urge the elongated cap 34 towards the battery unit 37 whereupon the contact pins 51 contact their counterpart contact pads 53 thereby energizing the LED 49 for delivering illumination light for intubation purposes.

While the invention has been described with respect to a limited number of embodiments, it will be appreciated that many variations, modifications, and other applications of the invention can be made within the scope of the appended claims.

We claim:

1. A laryngoscope handle for use with a laryngoscope blade having a tip, the handle having a leading end and a trailing end correspondingly adjacent and remote from a laryngoscope blade, the handle comprising a handle shell including
   i) a pair of opposite elongate semi-cylindrical handgrip support members, each member having two elongate edges that are permanently joined to the corresponding elongate edges of the other support member resulting in a tubular handgrip support having an internal bore;
   ii) a non-metal sleeve-like handgrip encircling said handgrip support; and
   iii) a rechargeable illumination unit including:
      a rechargeable battery;
      an illumination light source disposed toward the handle's leading end for selective illumination to provide illumination light at the laryngoscope blade's tip for illumination purposes;
      at least one user indication light source disposed toward the handle's trailing end for selective illumination to provide at least one visual user indication regarding the operability of said illumination unit during charging of same; and
      a light transmissive end cap at the handle's trailing end comprised of a light transmissive leading cylindrical portion that mounts into the trailing end of the handle, and a light transmissive trailing base portion that includes a light transmissive end section and a light transmissive axially extending wall section, wherein said light transmissive end cap glowing diffusely on interior illumination by said at least one user indication light source thereby facilitating user appraisal of the operability of said illumination unit.

2. The handle as claimed in claim 1 wherein said at least one visual user indication includes a first user indication for indicating said battery is charged to at least a predetermined minimum threshold and a second visual user indication for indicating said battery requires additional charging to reach said predetermined minimum threshold.

3. The handle as claimed in claim 2 wherein said at least one visual user indication includes a third visual user indication for indicating a fault condition of said illumination unit.

4. The handle as claimed in claim 1 wherein said handgrip support is made from metal support members.

5. The handle as claimed in claim 1 wherein said handgrip support is made from plastic support members.

6. The handle as claimed in claim 1 wherein said illumination unit is non-interchangeable.

7. The handle as claimed in claim 1 wherein said illumination unit is interchangeable on sliding insertion into said handle shell.

8. The laryngoscope handle as claimed in claim 1 in combination with a permanently mounted laryngoscope blade to said handle so as to constitute a single component laryngoscope.

9. The laryngoscope handle as claimed in claim 1 in combination with an interchangeable laryngoscope blade that can be snap fittingly mounted on the laryngoscope handle so as to constitute a dual component laryngoscope.

10. A rechargeable illumination unit for use in a laryngoscope including a laryngoscope handle and a laryngoscope blade with a tip, the laryngoscope handle having a leading end and a trailing end correspondingly adjacent and remote from the laryngoscope blade, the illumination unit comprising:
   (a) a rechargeable battery;
   (b) an illumination light source disposed toward the handle's leading end for selective illumination for providing illumination light at the laryngoscope blade's tip for illumination purposes;
   (c) at least one user indication light source disposed toward the handle's trailing end for selective illumination for providing at least one visual user indication regarding the operability of the illumination unit during charging of same; and
   (d) a light transmissive end cap at the handle's trailing end comprised of a light transmissive leading cylindrical portion that mounts into the trailing end of the handle, and a light transmissive trailing base portion that includes a light transmissive end section and a light transmissive axially extending wall section, wherein said light transmissive end cap glowing diffusely on interior illumination by said at least one user indication light source thereby facilitating user appraisal of the operability of the illumination unit.

11. The unit as claimed in claim 10 wherein said at least one visual user indication includes a first user indication for indicating said battery is charged to at least a predetermined minimum threshold and a second visual user indication for indicating said battery requires additional charging to reach said predetermined minimum threshold.

12. The unit as claimed in claim 11 wherein said at least one visual user indication includes a third visual user indication for indicating a fault condition of the illumination unit.

13. The interchangeable rechargeable illumination unit as claimed in claim 10 in combination with a rechargeable laryngoscope handle comprising a handle shell that can slidingly receive said unit that is slidingly inserted into said handle shell.

14. The unit as claimed in claim 13 in which said handle shell includes a pair of opposite semi-cylindrical metal handgrip support members permanently joined together to form a tubular handgrip support and a non-metal sleeve-like handgrip encircling said handgrip support.

15. The unit as claimed in claim 13 wherein said handle shell includes a pair of opposite semi-cylindrical plastic handgrip support members permanently joined together to form a tubular handgrip support and a non-metal sleeve-like handgrip encircling said handgrip support.

16. The unit as claimed in claim 10 in combination with a rechargeable laryngoscope handle for housing a non-interchangeable rechargeable illumination unit.

17. The unit as claimed in claim 10 in combination with a permanently mounted laryngoscope blade to a laryngoscope handle so as to constitute a single component laryngoscope.

18. The unit as claimed in claim 10 in combination with an interchangeable laryngoscope blade that can be snap fittingly mounted on a laryngoscope handle so as to constitute a dual component laryngoscope.

19. The unit as claimed in claim 10, wherein the laryngoscope handle has an internal bore and an exterior opening at the trailing end thereof; wherein the light transmissive end cap of said illumination unit is comprised of a leading light transmissive, cylindrical portion having an outer diameter such that the cylindrical portion can be received inside the internal bore of the handle, and having a pair of radial pins which extend radially outwardly from the cylindrical portion, and is comprised of an integral, light transmissive trailing cylindrical base having an outer diameter and configuration so as to be the same as the outer diameter and configuration of the handle; and wherein a wall defining the handle bore has peripheral grooves that removably receive the radial pins and mount the end cap onto the handle.

20. A laryngoscope handle for use with a laryngoscope blade having a tip, the handle having a leading end and a trailing end correspondingly adjacent and remote from a laryngoscope blade, the handle comprising a handle shell including
  i) a pair of opposite elongate semi-cylindrical handgrip support members, each member having two elongate edges that are permanently joined to the corresponding elongate edges of the other support member resulting in a tubular handgrip support having an internal bore;
  ii) a non-metal sleeve-like handgrip encircling said handgrip support; and
  iii) a rechargeable illumination unit including:
    a rechargeable battery;
    an illumination light source disposed toward the handle's leading end for selective illumination to provide illumination light at the laryngoscope blade's tip for illumination purposes;
    at least one user indication light source disposed toward the handle's trailing end for selective illumination to provide at least one visual user indication regarding the operability of said illumination unit during charging of same; and
    a light transmissive end cap at the handle's trailing end glowing diffusely on interior illumination by said at least one user indication light source thereby facilitating user appraisal of the operability of said illumination unit; wherein said light transmissive end cap of said illumination unit is comprised of a leading light transmissive, cylindrical portion having an outer diameter such that the cylindrical portion can be received inside the bore of the handgrip support, and having a pair of radial pins which extend radially outwardly from the cylindrical portion, and is comprised of an integral, light transmissive trailing cylindrical base having an outer diameter and configuration so as to be the same as the outer diameter and configuration of the handgrip; and wherein the handgrip support has peripheral grooves that removably receive the radial pins and mount the end cap onto the handle.

* * * * *